United States Patent
Cusola Aumedes et al.

(10) Patent No.: US 9,702,087 B2
(45) Date of Patent: Jul. 11, 2017

(54) ISOLATED AQUEOUS ENZYMATIC PREPARATION AND THE USE THEREOF FOR THE FUNCTIONALIZATION OF THE SURFACE OF PAPER OR CELLULOSIC SUBSTRATES

(71) Applicant: UNIVERSITAT POLITECNICA DE CATALUNYA, Barcelona (ES)

(72) Inventors: Oriol Cusola Aumedes, Barcelona (ES); M. Blanca Roncero Vivero, Barcelona (ES); Cristina Valls Vidal, Barcelona (ES); Teresa Vidal Llucia, Barcelona (ES)

(73) Assignees: Universitat Politecnica de Catalunya, Barcelona (ES); Nopco Paper Technology Holding AS, Drammen (NO)

( * ) Notice: Subject to any disclaimer, the term of this patent is extended or adjusted under 35 U.S.C. 154(b) by 227 days.

(21) Appl. No.: 14/405,232

(22) PCT Filed: Jun. 3, 2013

(86) PCT No.: PCT/ES2013/070355
§ 371 (c)(1),
(2) Date: Feb. 23, 2015

(87) PCT Pub. No.: WO2013/182723
PCT Pub. Date: Dec. 12, 2013

(65) Prior Publication Data
US 2015/0167246 A1    Jun. 18, 2015

(30) Foreign Application Priority Data
Jun. 4, 2012 (ES) .................................. 201230852

(51) Int. Cl.
| | | |
|---|---|---|
| *A61K 38/43* | (2006.01) | |
| *D21H 19/12* | (2006.01) | |
| *D21H 25/02* | (2006.01) | |
| *D21H 17/00* | (2006.01) | |
| *D21H 17/06* | (2006.01) | |
| *D21H 21/14* | (2006.01) | |
| *D21H 21/16* | (2006.01) | |
| *B05D 1/02* | (2006.01) | |
| *B05D 1/18* | (2006.01) | |
| *D21H 17/14* | (2006.01) | |
| *C12N 9/02* | (2006.01) | |

(52) U.S. Cl.
CPC ............. *D21H 19/12* (2013.01); *B05D 1/02* (2013.01); *B05D 1/18* (2013.01); *C12N 9/0061* (2013.01); *C12Y 110/03002* (2013.01); *D21H 17/005* (2013.01); *D21H 17/06* (2013.01); *D21H 17/14* (2013.01); *D21H 21/14* (2013.01); *D21H 21/16* (2013.01); *D21H 25/02* (2013.01)

(58) Field of Classification Search
None
See application file for complete search history.

(56) References Cited

U.S. PATENT DOCUMENTS 6,610,172 B1    8/2003  Lund

FOREIGN PATENT DOCUMENTS

| ES | 2352495 | 2/2011 |
| WO | 2005061791 A1 | 7/2005 |
| WO | 2011009979 | 1/2011 |
| WO | 2011073531 A1 | 6/2011 |

OTHER PUBLICATIONS

Fried Experientia (1971) 27(2): 123-125.*
Hossain et al. J. Biotecnol. (2009) 141: 58-63.*
Aracri, E., et al., "Application of laccase—natural mediator systems to sisal pulp: An effective approach to biobleaching or functionalizing pulp fibres," 2009, pp. 5911-5916, vol. 100, Bioresource Technology, Elsevier.
Fillat, A., et al., "A new approach to the biobleaching of flax pulp with laccase using natural mediators," 2010, pp. 4104-4110, vol. 101, Bioresource Technology, Elsevier.
Garcia-Ubasart, J., et al., "A new procedure for the hydrophobization of cellulose fibre using laccase and a hydrophobic phenolic compound," 2012, pp. 341-344, vol. 112, Bioresource Technology, Elsevier.
Garcia-Ubasart, J., et al., "Enzymatic treatments of pulp using laccase and hydrophobic compounds," 2011, pp. 2799-2803, vol. 102, No. 3, Bioresource Technology, Elsevier.
Hossain, H.M., et al., "Hydrophobic property of handmade jute paper treated by sizing material 'rosin'," Jan. 2010, pp. 48-52, vol. 5, No. 1, Daffodil International University Journal of Science and Technology.
Hossain, Kh. M., et al., "Enzyme-mediated coupling of a bi-functional phenolic compound onto wool to ehance its physical, mechanical and functional properties," 2010, pp. 326-330, vol. 46, Enzyme and Microbial Technology, Elsevier.
Hubbe, M., "Paper's resistance to wetting—a review of internal sizing chemicals and their effects," 2006, pp. 106-145, vol. 2, No. 1, BioResources.
International Preliminary Report and Written Opinion for International Application No. PCT/ES2013/070355 mailed Dec. 9, 2014.
International Search Report for International Application No. PCT/ES2013/070355 mailed Sep. 16, 2013.

(Continued)

*Primary Examiner* — Susan Hanley
(74) *Attorney, Agent, or Firm* — RatnerPrestia

(57) ABSTRACT

In a first aspect, the present invention relates to an isolated aqueous enzymatic preparation obtained from the reaction of at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group. In a second aspect, the present invention relates to the use of said isolated aqueous enzymatic preparation in the functionalization of the surface of paper or cellulosic substrates.

8 Claims, 4 Drawing Sheets

(56) References Cited

OTHER PUBLICATIONS

Kudanga, T., et al., "Laccase-mediated wood surface functionalization," 2008, pp. 297-302, vol. 8, No. 3, Engineering in Life Sciences.

Moldes, D., et al., "Comparative study of the efficiency of synthetic and natural mediators in laccase-assisted bleaching of eucalyptus kraft pulp," 2008, pp. 7959-7965, vol. 99, Bioresource Technology, Elsevier.

Neimo, L., "Internal sizing of paper," 1999, pp. 151-203, vol. 4, Papermaking Science and Technology, Papermaking Chemistry.

Ozdemir, M., et al., "Active food packaging technologies," 2004, pp. 185-193, vol. 44, Critical Reviews in Food Science and Nutrition.

Serpen, A., et al., "A new procedure to measure the antioxidant activity of insoluble food components", 2007, pp. 7676-7681, vol. 55, Journal of Agricultural and Food Chemistry.

van den Berg, R., et al., "Applicability of an improved Trolox equivalent antioxidant capacity (TEAC) assay for evaluation of antioxidant capacity measurements of mixtures," 1999, pp. 511-517, vol. 66, Food Chemistry, Elsevier.

European Office Action issued in EP 13 800 801.6 dated Feb. 3, 2017, 7 pages.

Cusola et al., Application of surface enzyme treatments using laccase and a hydrophobic compound to paper-based media, Bioresource Technology 131 (2013) pp. 521-526.

Cusola et al., Enzymatic treatments of paper surface using laccase, hydrophobic compounds and lignin, 5th International Colloquium on Eucalyptus Pulp, May 9-12, 2011. Porto Segura, Bahia, Brazil, 5 pages \* cited by examiner

ISOLATED AQUEOUS ENZYMATIC PREPARATION AND THE USE THEREOF FOR THE FUNCTIONALIZATION OF THE SURFACE OF PAPER OR CELLULOSIC SUBSTRATES

CROSS-REFERENCE TO RELATED APPLICATIONS

This application is a national stage of International application No. PCT/ES2013/070355, filed Jun. 3, 2013, and claiming priority of Spanish application No. P201230852, filed Jun. 4, 2012. The disclosures of each of these applications are incorporated herein by reference in their entirety for all purposes.

FIELD OF THE INVENTION

The present invention preferably relates to the field of paper and cellulosic substrates. The present invention particularly relates to an isolated aqueous enzymatic preparation and to the use thereof for the functionalization of the surface of paper or cellulosic substrates.

BACKGROUND OF THE INVENTION

Functionalization consists of adding functional chemical groups on a surface for the purpose of modifying or improving its properties. Some of these properties can be hydrophobicity, antioxidant and/or bacteriostatic capacity, high mechanical strengths, etc. As regards the property of hydrophobicity, the absorption of liquids in the structure of the paper is a key factor for the final use of paper products (e.g. paper cups, paper bags, boxes for packaging or containers for liquids), and also for runnability of paper-making processes, e.g., in size press or printing (1, 2). Paper manufacturers perform processes to reduce the rate of liquid absorption into the structure of the paper by treating the fibrous suspension with hydrophobic substances (3); this operation is referred to as "internal sizing". In contrast with internal sizing is "external sizing", the purpose of which is to improve surface properties (such as smoothness, permeability, printability, etc) of the substrate for subsequent use thereof in different processes, e.g., papers for printing and writing. This process consists of applying chemicals (e.g. starch among others) on the surface of the paper (size press, coating, etc) during the paper manufacturing process. With respect to the antioxidant and antimicrobial capacities, many foods are known to deteriorate and lose quality during transport, processing and storage, said foods being contaminated through microorganisms, chemical reactions and physical changes. Among these degradation models, microbial deterioration and oxidation reactions have the greatest impact. The antioxidant and antimicrobial property in paper is of interest from the viewpoint of food preservation, because paper with antioxidant or antimicrobial properties could be implemented in manufacturing a containment packaging with advanced properties (4).

The specific case of functionalizing individual cellulose fibers by means of biotechnological processes using enzymes has already been described, for example, for the hydrophobization of fibers (5), or the incorporation of natural phenols susceptible to conferring antioxidant properties or bacteriostatic properties, or to increasing mechanical strength (6). In fact, there are two patents where an oxidoreductase enzyme (laccase) is applied directly to the suspension of fibers, i.e., before the substrate is formed. One of these patents is for improving the wet strength of the paper (U.S. Pat. No. 6,610,172 B1), and the other patent is for the internal sizing of the paper (WO 11/009,979). These enzymatic treatments in the paper-making industry are designed for being applied on the fibrous suspension, in the mixing boxes and before forming the sheet. This entails several drawbacks from the industrial viewpoint, such as, for example: i) a limitation in the work conditions (pH, temperature, consistency, reaction time, etc) which must be suitable for optimal enzyme action, ii) high consumption of the transferred reagent, iii) possible interferences in bonds between fibers or with other products of the process, and iv) difficulty in recirculating the generated effluents. These drawbacks mean that said enzymatic treatments described up until now are industrially unfeasible.

A possible solution that would reduce transferred reagent consumption, would not affect the binding capacity between fibers and would eliminate the difficulty in recirculating the effluents would be to perform enzymatic treatments on the surface of the cellulosic substrate instead of on the fibrous suspension. However, performing an enzymatic treatment directly on the surface of a cellulosic substrate is unfeasible due to the conditions under which the enzymatic reaction must take place, such as long reaction times, for example. In fact, the literature does not describe any application of enzymatic systems for functionalization purposes that is applied directly on the surface of paper in the forming table, before drying, or once the sheet has already been formed. There are references about surface biotreatments in wood (7) and in finished fabrics (8). Nevertheless, in these treatments the presence of the substrate (wood or fabric) is necessary at the time of the enzymatic reaction. For a paper-making process, there are no references to surface biotreatments applied on the paper, i.e., on a previously formed sheet.

Therefore, for the purpose of overcoming the drawbacks indicated above, the authors of the present invention provide a new product, called post-enzymatic preparation, for the application thereof directly on the surface of the cellulosic substrate that has already been formed, providing the following advantages:

1.—This product is a simple and versatile formulation that is easy to apply on the surface of the cellulosic substrate.
2.—Different post-enzymatic preparations or products can be prepared for conferring different properties to the substrate by changing only natural or synthetic compound/compounds in the formulation.
3.—The conditions of the enzymatic process do not vary much according to the natural or synthetic compound.
4.—This formulation therefore varies according to the final property to be acquired in the substrate, but without needing to modify reaction conditions, depending only on whether or not the techniques for facilitating disaggregation/dispersion of the compound to be transferred are needed.
5.—It need not be prepared in-situ at the time of being applied, so it can be supplied as a formulated product.
6.—The enzymatic reaction in preparing the product to be applied takes place before being used on the substrate, allowing application thereof on the surface at different points of the paper machine, such as for example in the forming table, before the drying section, after the drying section and even in the finished product.
7.—The high temperature conditions in the paper machine do not affect/jeopardize the enzymatic reaction because said reaction takes place outside the point of application, and therefore outside the process of manufacturing the substrate.

8.—Since the product is not applied until the sheet is already formed, the enzymatic treatment does not affect the binding capacity of the fibers or the process itself for forming the sheet of paper.

9.—Since this post-enzymatic product can be applied on the surface, the amounts of natural or synthetic compound are reduced, and furthermore said compound stays more on the surface, therefore being more effective.

10.—The rheological properties of the post-enzymatic preparation allow it to be applied on the surface by means of different methods: size press, sprayers, metering bar, immersion-impregnation, etc.

11.—The use of this product in the mill does not involve an additional investment in machinery because systems already existing in the paper machine can be used, and if that is not the case, the investment is not disproportionate because only sprayers and a storage tank for the post-enzymatic preparation would be needed.

12.—The product can be prepared in concentrated form to subsequently be diluted right before use, thereby reducing transport and storage costs, the size of the facilities for preparing the product and the energy consumed for preparing it.

The product of the present invention therefore allows providing the substrate with different properties according to the natural or synthetic compound used in the formulation of the product. This innovative product consists of a "post-enzymatic" preparation, i.e., it is a preparation resulting from an enzymatic reaction, the final rheological conditions and characteristics of which allow it to subsequently be applied on the surface by means of different metering system, without interfering in the process of manufacturing the substrate.

The authors of the present invention previously patented according to patent document ES2352495B1 a method in which internal sizing of paper was achieved by means of an enzyme-mediator system. As indicated in the examples of said patent, the process consisted of previously mixing the cellulose fibers (which will subsequently form the paper) with a compound (mediator), and subsequently adding a laccase-type enzyme so that the enzymatic reaction takes place for a specific time in the presence of the cellulose fibers, and thereby developing the property of internal sizing in the paper once it is formed. Therefore, the earlier patent did not describe the isolated product of the present invention, which is the result of the reaction of a compound, as defined in the present invention, and an oxidoreductase enzyme, without the presence of cellulose fibers. Furthermore, this described product which is obtained once the enzymatic reaction has ended is applied on the surface of the substrate, and furthermore provides different properties.

The present invention allows obtaining a product derived from the enzymatic reaction without the presence of cellulose fibers (an external agent in general) and outside the paper manufacturing process, being able to subsequently apply the product on the surface of the paper. Therefore, this product can be manufactured outside the paper-making industry as a chemical additive and subsequently be used by the paper-making company, using current technology and without jeopardizing the process of manufacturing the substrate.

Additionally, unlike the earlier patent (ES2352495B1), the product obtained in the present invention is a preparation (post-enzymatic product) derived from the enzymatic reaction; in contrast, the product obtained in ES2352495B1 consists of modified cellulose fibers in an aqueous suspension the production of which has always been within the process of manufacturing paper, entailing significant drawbacks making the industrial application thereof unfeasible. However, the present invention does not involve any drawback for being applied on an industrial level.

In addition, the earlier patent (ES2352495B1) mentions producing an internal sizing, whereas different properties (hydrophobicity, antioxidant and antimicrobial capacity, wet strength, among others) are achieved in the present invention.

SUMMARY OF THE INVENTION

Figure 1:
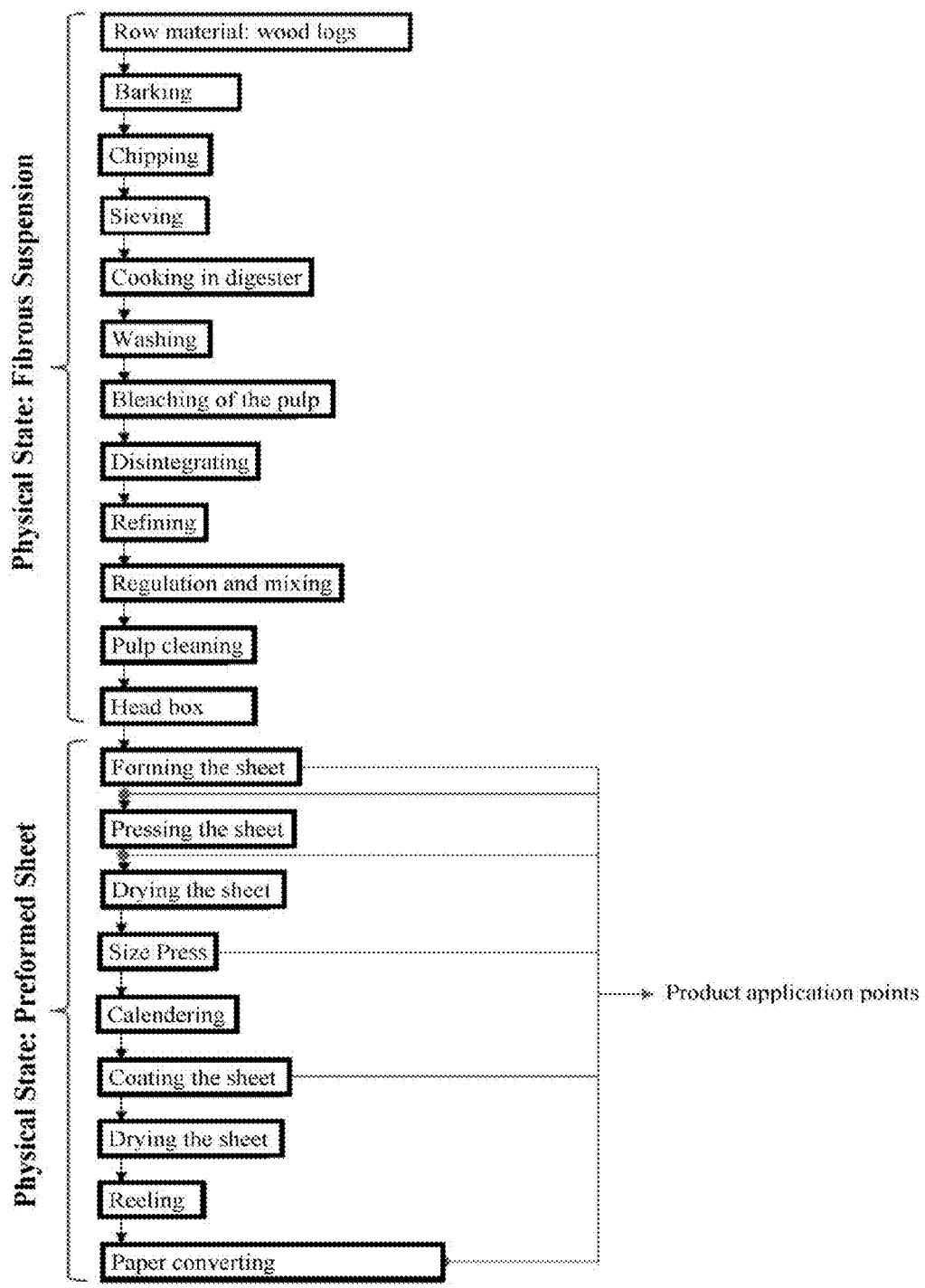
FIG. 1 depicts a block diagram of a paper mill.

In a first aspect, the present invention relates to an isolated aqueous enzymatic preparation obtained from the reaction of at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group, characterized in that the reaction is performed in the absence of an external agent (e.g. cellulose fibers).

In a second aspect, the present invention relates to the surface application of the post-enzymatic product obtained after the end of the reaction of at least one oxidoreductase enzyme and at least one natural or synthetic product comprising, in the structure thereof, at least one phenol or alcohol group, which optionally has one or more hydrophobic chains, or at least one sterol group, for the functionalization of the surface of paper or cellulosic substrates.

DETAILED DESCRIPTION OF THE INVENTION

In a first aspect, the present invention relates to an isolated aqueous enzymatic preparation obtained from the reaction of at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group, characterized in that the reaction is performed in the absence of an external agent (e.g. cellulose fibers). Said isolated aqueous enzymatic preparation is also referred to in the present invention as "post-enzymatic product or preparation" because it is a preparation resulting from an enzymatic reaction.

Said natural or synthetic compound is preferably selected from the group consisting of the following structures:

Structure A

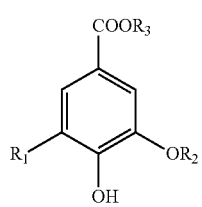

where $R_3$ can be —H or an alkyl$\geq C_1$, preferably between $C_1$ and $C_{34}$, and $R_1$, $R_2$ can be:
  i) $R_1$=—OH and $R_2$=—H;
  ii) $R_1$ and $R_2$=—H, 3,4-dihydroxy-benzoic acid esters; or
  iii) $R_1$=—H and $R_2$=—CH$_3$, vanillic acid esters Structure B-1: Tocopherol

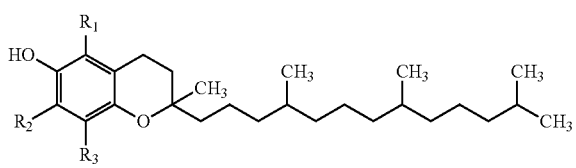

where $R_1$, $R_2$ and $R_3$ can be:
  i) $R_1$=$R_2$=$R_3$=—CH$_3$;
  ii) $R_1$=$R_3$=—CH$_3$; $R_2$=—H;
  iii) $R_2$=$R_3$=—CH$_3$; $R_1$=—H; or
  iv) $R_1$=$R_2$=—H; $R_3$=—CH$_3$ Structure B-2: Tocotrienols

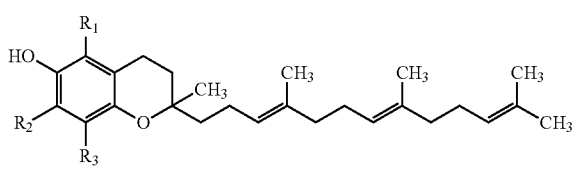

where $R_1$, $R_2$ and $R_3$ can be:
  i) $R_1$=$R_2$=$R_3$=—CH$_3$;
  ii) $R_1$=$R_3$=—CH$_3$; $R_2$=—H;
  iii) $R_2$=$R_3$=—CH$_3$; $R_1$=—H; or
  iv) $R_1$=$R_2$=—H; $R_3$=—CH$_3$ Structure C

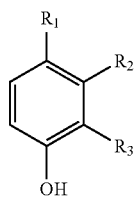

where $R_1$, $R_2$ and $R_3$ can be:
  i) $R_1$=—H, $R_3$=—OH and $R_2$=alkyl$\geq C_1$, preferably between $C_1$ and $C_{34}$;
  ii) $R_2$=—H, $R_3$=—OH and $R_1$=alkyl$\geq C_1$, preferably between $C_1$ and $C_{34}$; or
  iii) $R_3$=—H, $R_3$=—H and $R_2$=alkyl$\geq C_1$, preferably between $C_1$ and $C_{34}$ Structure D: 2,4,6-tris(1-phenylethyl)phenol

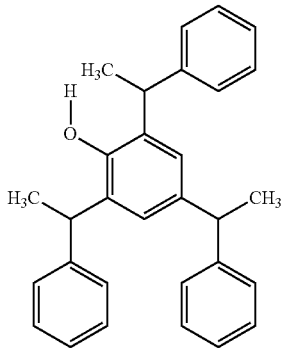 [SMILES: CC(c1ccccc1)c1cc(C(C)c2ccccc2)c(O)c(C(C)c2ccccc2)c1]

Structure E: 4-[4-(trifluoromethyl)phenoxy]phenol

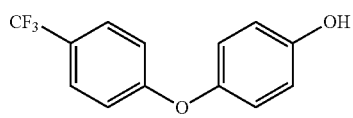 [SMILES: Oc1ccc(Oc2ccc(C(F)(F)F)cc2)cc1]

In the preceding structures, the term "alkyl" is understood to include either aliphatic or alicyclic linear and branched alkyl groups, and they can in turn be saturated or unsaturated (for example, partially unsaturated or completely unsaturated) having at least one carbon atom in the structure, preferably between 1 ($C_1$) and 34 ($C_{34}$) carbon atoms in the structure. Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$). Examples of saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

Preferred examples of natural or synthetic compounds which, after the enzymatic reaction, provide the resulting preparation with the capacity to confer hydrophobic properties are:

dodecyl 3,4,5-trihydroxybenzoate (lauryl gallate)
3,4,5-trihydroxybenzoic acid octyl ester (octyl gallate)
ethyl 3,4,5-trihydroxybenzoate (ethyl gallate)
propyl 3,4,5-trihydroxybenzoate (propyl gallate)
(E)-3-(4-hydroxy-3-methoxyphenyl)prop-2-enoic acid (ferulic acid)
(2R)-2,5,7,8-tetramethyl-2-[(4R,8R)-(4,8,12-trimethyltridecyl)]-6-chromanol (alpha tocopherol)
2,4,6-tris(1-phenylethyl)phenol (tristyrylphenol)
1-(4-hydroxy-3-methoxyphenyl)ethanone (acetovanillone)
3-(4-hydroxy-3,5-dimethoxyphenyl)prop-2-enal (sinapylaldehyde)
distilled cashew nut shell liquid (cardanol)

Preferred examples of natural or synthetic compounds which, after the enzymatic reaction, provide the resulting preparation with the capacity to confer antioxidant properties are:

1-(4-hydroxy-3-methoxyphenyl)ethanone (acetovanillone)
3-(4-hydroxy-3,5-dimethoxyphenyl)prop-2-enal (sinapylaldehyde)
ethyl 3,4,5-trihydroxybenzoate (ethyl gallate)
3,4,5-trihydroxybenzoic acid octyl ester (octyl gallate)
dodecyl 3,4,5-trihydroxybenzoate (lauryl gallate)
propyl 3,4,5-trihydroxybenzoate (propyl gallate)
(2R)-2,5,7,8-tetramethyl-2-[(4R,8R)-(4,8,12-trimethyltridecyl)]-6-chromanol (alpha tocopherol)
2,4,6-tris(1-phenylethyl)phenol (tristyrylphenol)
3-(3,4-dihydroxyphenyl)-2-propenoic acid (caffeic acid)
4-hydroxybenzoic acid (para-hydroxybenzoic acid)
3,4,5-trihydroxybenzoic acid (gallic acid)
4'-hydroxy-3',5'-dimethoxyacetophenone (acetosyringone),
4-hydroxy-3,5-dimethoxybenzaldehyde (syringaldehyde)
(E)-3-(4-hydroxyphenyl)-2-propenoic acid (para-coumaric acid)
4-hydroxy-3-methoxybenzaldehyde (vanillin)
(E)-3-(4-hydroxy-3-methoxyphenyl)prop-2-enoic acid (ferulic acid)
(E)-3-(4-hydroxy-3-methoxyphenyl)prop-2-enal (coniferyl aldehyde)
3-(4-hydroxy-3,5-dimethoxyphenyl)prop-2-enoic acid (sinapic acid)
2,4,5,6(1H,3H)-pyrimidinetetrone 5-oxime (violuric acid)
methyl 4-hydroxy-3,5-dimethoxybenzoate (methyl syringate)
17-(5-ethyl-6-methylheptane-2-yl)-10,13-dimethyl-2,3,4,7,8,9,11,12,14,15,16,17-dodecahydro-1H-cyclopenta[a]phenanthren-3-ol (β-sitosterol)
4-[4-(trifluoromethyl)phenoxy]phenol
3-methylbutyl o-hydroxybenzoate (isoamyl salicylate)

Preferred examples of natural or synthetic compounds which, after the enzymatic reaction, provide the resulting preparation with the capacity to confer antimicrobial properties are:

dodecyl 3,4,5-trihydroxybenzoate (lauryl gallate)
4-hydroxy-3,5-dimethoxybenzaldehyde (syringaldehyde)
4'-hydroxy-3',5'-dimethoxyacetophenone (acetosyringone)
(E)-3-(4-hydroxyphenyl)-2-propenoic acid (para-coumaric acid)

The dose of enzyme to be used is between a minimum of 20 U/L and a maximum which depends on the concentration of the natural or synthetic product used; the enzyme dose range is preferably between 50 U/L and 3000 U/L.

The natural or synthetic compound that is reacted is applied at doses that depend on the solubility of the compound and on the degree of the property to be achieved. Said dosage range is between a minimum of 0.1 g/L and a maximum that depends on the following factors: product solubility and the maximum amount of product that can be kept in homogenous suspension, either by means of stable emulsion or by means of stirring. The dosage range is preferably between 0.1 and 30 g/L. The natural or synthetic compound is selected according to the properties to be conferred by the post-enzymatic preparation. Some examples of properties are: hydrophobicity, antioxidant power, bactericidal capacity, antimicrobial capacity, gas barrier property, water, or generally liquid, barrier property and oil or fat barrier property.

In a preferred embodiment, the isolated aqueous enzymatic preparation is obtained by means of the reaction of at least two natural or synthetic compounds with at least one oxidoreductase enzyme, to therefore confer various properties to the paper and the cellulosic substrates based on a single post-enzymatic preparation.

The time of duration of the isolated aqueous enzymatic preparation depends on the combination of enzyme and natural or synthetic compound used.

The enzymatic treatments can be performed under pressure or at atmospheric pressure according to enzyme efficiency or needs.

In a preferred embodiment, the isolated aqueous enzymatic preparation of the present invention is obtained from the reaction of at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group, at a pH between 4 and 10, and a temperature between room temperature and 90° C. Said pH preferably ranges between 4 and 7. Said temperature also preferably ranges between 30° C. and 60° C.

If the natural or synthetic compound that is reacted with the enzyme is insoluble in aqueous medium, several techniques can be used to obtain good disaggregation/dispersion. The following can be highlighted among such techniques:

Ultrasonic disintegration: To break up the aggregates of insoluble compounds, before performing the enzymatic reaction, an ultrasonic tip is submerged in an aqueous enzymatic preparation comprising the insoluble compound. Any ultrasonic tip can be used, therefore the sonication power level and reaction time are established according to the tip used and the disaggregation complexity of the compound. A smaller particle size and a more homogenous distribution of the insoluble compound are obtained with this technique.

Use of a natural or synthetic surfactant: In the isolated aqueous enzymatic preparation according to the first aspect of the invention, it may be necessary to add a natural or synthetic surfactant to reduce the surface tension of the reaction preparation and improve distribution of the insoluble compound. The dose to be used depends on the type of surfactant and on the natural or synthetic compound. As previously indicated, said surfactant is ionic, more preferably anionic, and an example of a surfactant useful in the present invention is lignin sulfonate.

Therefore, in a preferred embodiment, in the reaction for obtaining the enzymatic preparation of the present invention between at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group, a natural or synthetic surfactant is also added for facilitating disaggregation/dispersion of the natural or synthetic compound before the reaction with the enzyme. Said surfactant is preferably ionic, more preferably anionic. An example of a surfactant useful in the present invention is lignin sulfonate.

In another preferred embodiment, in the reaction for obtaining the enzymatic preparation of the present invention between at least one oxidoreductase enzyme, preferably a laccase, and at least one natural or synthetic product, preferably a natural compound, said natural or synthetic product comprising, in the structure thereof, at least one phenol or alcohol group, which optionally has one or more hydrophobic chains, or at least one sterol group, ultrasounds are used for disaggregating/dispersing the natural or synthetic compound prior to reaction with the enzyme.

In a preferred embodiment, ultrasonic disintegration is performed first and then the addition of a surfactant is performed.

The ultrasonic disintegration and/or the addition of a surfactant are always carried out before addition of the enzyme.

Once the isolated aqueous post-enzymatic preparation has been obtained, it can be stored for subsequent use.

This post-enzymatic product can be obtained in concentrated form, using high concentrations of the initial components, such that it can be prepared, transported and/or stored in small volumes and can subsequently be diluted right before being used. The degree of dilution will be determined by the level or amount of the property to be obtained.

It should be pointed out that unlike other products of the state of the art, this post-enzymatic product is obtained without the presence of cellulose fibers (or any external agent in general) and outside the paper manufacturing process, being able to subsequently be applied on the surface of paper (see below in use thereof). Therefore, this product can be manufactured outside the paper-making industry as a chemical additive and subsequently be used by a paper manufacturing company, without modifying or interfering in the process of manufacturing the substrate.

Additionally, the product of the present invention is distributed on the surface of paper once it is applied (see below in use thereof).

Another aspect of the invention relates to the use of an isolated aqueous post-enzymatic preparation obtained from the reaction of at least one oxidoreductase enzyme and at least one natural or synthetic product comprising, in the structure thereof, at least one phenol or alcohol group, which optionally has one or more hydrophobic chains, or at least one sterol group, and any of the preferred variants thereof, in the functionalization of the surface of paper or cellulosic substrates. Said functionalization of the surface is achieved by means of applying said post-enzymatic product on the surface of paper or cellulosic substrates.

The cellulosic substrate useful in the present invention includes, but is not limited to, substrate obtained from wood and non-wood fibers, bleached and non-bleached fibers, mechanical, chemical and semi-chemical pulps, recycled fibers, cellulose microfiber films, cellulose nanofiber films, nanocellulose crystals, lignin films or other types of films and substrates. Furthermore, commercial substrates can also be used.

Different techniques can be used to modify the ionic surface charge of the cellulosic substrate and therefore improve fixing of the post-enzymatic product on the surface thereof. Specifically, treatments with cationic products such as cationic polyamidoamine-epichlorohydrin (PAAE) resins, chitosan, cationic starch or others are performed for fixing of some post-enzymatic products.

In a preferred embodiment, the aqueous enzymatic preparation of the present invention is applied on the surface of paper or cellulosic substrates by means of immersion-impregnation, spraying, size press, metering bar, among others, which are surface application techniques commonly used in manufacturing cellulosic substrates. Once the paper or substrate has come into contact with the aqueous post-enzymatic product, it is left to dry completely at room temperature or under heat.

The size press consists of two horizontally arranged rolls applying a specific pressure together. The liquid to be transferred to the paper or substrate is arranged on the upper contact side, and this liquid passes through the cylinders. The liquid is therefore transferred onto the surface of the paper or substrate. The parameters affecting the transferred liquid amount are speed and pressure.

The sprayers consist of sprayer heads where the liquid to be transferred is sent at a high pressure, and due to the geometry of the outlet holes, they generate microdrops that are deposited in the form of a thin layer on the paper or substrate.

The metering bar consists of a rotating cylinder immersed in a vessel with the preparation to be transferred to the paper or substrate, such that a certain amount of product is arranged on one of the faces of the paper or substrate. A second grooved and calibrated cylinder (metering bar) then removes the excess product, leaving the desired product thickness. Treatment is only performed on one of the faces of the paper or substrate in this system.

In the immersion-impregnation process, the paper or substrate is submerged in and made to pass through a vessel filled with the liquid to be transferred to the paper or substrate. The rate of passage and the exposed surface will determine the amount of product that is absorbed. Metering bars can be arranged at the outlet to control the excess transferred liquid.

In another preferred embodiment, the aqueous enzymatic preparation is applied on the paper or cellulosic substrates in the forming area, in the drying section, in the size press, in the coating area, in the end product, or between said operations (FIG. 1).

A set of examples which only intend to illustrate the invention without limiting the scope thereof are provided below.

Example 1

The present example illustrates obtaining a product which, when applied on the surface of the pre-formed or finished substrate, increases the hydrophobic character of said substrate. Said product consists of a post-enzymatic preparation using a laccase enzyme of *Trametes villosa* and lauryl gallate (LG) as the hydrophobic compound.

Doses and Conditions for Obtaining the Post-Enzymatic Product

The enzyme used was the laccase of *Trametes villosa* with an activity of 588 U/mL.

In this specific case, the treatments were performed in a 250 mL reactor, hermetically closed and stirred continuously. General reaction conditions were: pH 4, 0.12% lauryl gallate (hydrophobic compound), amount of surfactant 0.12%, which in this case was lignin sulfonate, temperature 40° C. and a 4-hour reaction time. After the reaction, the post-enzymatic product obtained was stored for subsequent surface application. The following table shows the treatment doses used for obtaining the functionalization preparation (post-enzymatic product), as well as the different controls performed:

TABLE 1

Treatment doses

| Treatment | Enzyme doses (mL) | Lauryl gallate doses (LG) (g) | Surfactant (lignin sulfonate) doses (g) | Water pH 4 doses (mL) |
|---|---|---|---|---|
| A | 0.00 | 0.06 | 0.00 | 49.94 |
| B | 0.00 | 0.06 | 0.06 | 49.88 |
| C | 0.00 | 0.00 | 0.06 | 49.94 |
| D | 0.102 | 0.06 | 0.00 | 49.84 |
| E | 0.102 | 0.00 | 0.06 | 49.84 |
| F | 0.102 | 0.06 | 0.06 | 49.78 |

Hydrophobicity Study

The Tappi standard T835 om-08 water drop test (WDT) was initially performed to determine hydrophobicity of the papers in a simple manner. This test consists of applying a distilled water drop by means of a syringe and measuring the time it takes to be adsorbed by the paper.

The initial contact angle between a water drop and the surface of treated papers and a model of the absorption-evaporation of the water drop in the structure of the paper were also analyzed.

Application of the Post-Enzymatic Product. Results.

The post-enzymatic solutions obtained according to Table 1 were applied were applied on the surface of the substrate (in this case, commercial filter paper) and progression of the WDT was measured (as an indicator of the degree of hydrophobicity). Said surface application was performed by immersion. The WDT results are shown in Table 2.

TABLE 2

WDT of the impregnated samples

| Paper impregnated with the product | Absorption time (WDT) (s) |
|---|---|
| A | 5 ± 1 |
| B | 6 ± 1 |
| C | 5 ± 1 |
| D | 187 ± 16 |
| E | 5 ± 1 |
| F | 3800 ± 213 |

Even when use of the post-enzymatic product obtained from combining lauryl gallate (LG) and the enzyme causes a significant increase in hydrophobicity (treatment D, Tables 1 and 2), it can be seen that the substantial increase in said property is clearly produced with the post-enzymatic product resulting from the reaction between the three elements, i.e., LG, surfactant and enzyme (treatment F, Tables 1 and 2). The other controls performed (A, B, C and E) do not produce an increase in hydrophobicity in the substrates.

The addition of lignin sulfonate as a surfactant when preparing the post-enzymatic product has a key effect on the improvement of hydrophobicity in the substrate. This substantial improvement can be attributed to better distribution of the hydrophobic product (LG) over the surface of the substrate. This represents a novelty because the use of lignin sulfonate as a surfactant for improving the distribution of hydrophobic products for functionalization has not been described up until now. The addition of lignin sulfonate also helps to maintain the dispersion of LG in its oxidized form and to preserve stability of the functionalizing preparation over time.

Effect of Ultrasonic Disintegration

The phenol compound LG is a solid with a very low surface free energy that tends to form aggregates and is not wetted by water, resulting in nil dispersion in the aqueous medium. Using ultrasounds causes these aggregates to break apart and forces the LG particles to be introduced in the aqueous medium. As a result of applying ultrasounds, LG is homogenously distributed throughout the medium, but enzymatic treatment must be performed immediately because LG will otherwise precipitate and tend to form aggregates again.

Effect of Heat Treatment and Doses on Hydrophobicity

Figure 2:
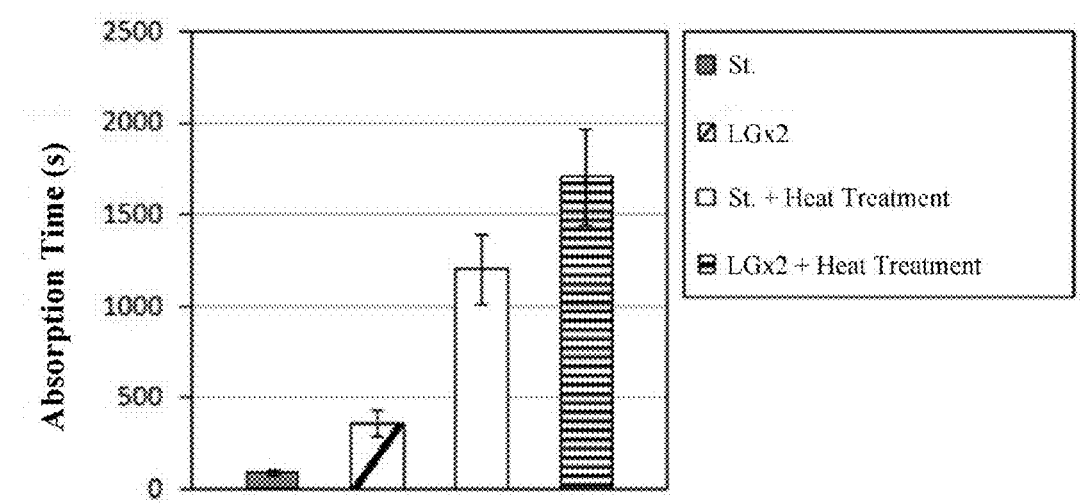
FIG. 2 shows the progression of the hydrophobic property measured from the WDT by varying process conditions. St. refers to standard treatment; LGx2 refers to the standard treatment doubling the phenol compound dose; St.+Heat treatment refers to the standard treatment applying curing at temperature; LGx2+Heat treatment refers to the combination of the curing and the doubling of the phenol compound dose.

Different tests were performed by doubling the phenol compound dose and applying heat treatment to functionalized papers to see the effect of the variation of these parameters on hydrophobicity. A standard treatment modified as indicated was performed. The standard treatment was performed with the following conditions: pH 4, amount of phenol compound 0.12%, amount of surfactant 0.12%, temperature 40° C., time 1 hour. FIG. 2 shows that both doubling the phenol compound dose and the heat treatment cause an increase in hydrophobicity, and that they both have a synergistic effect when they are applied together.

Contact Angle and Absorption

Figure 3:
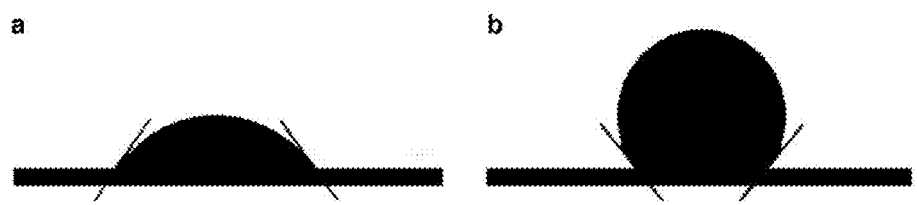
FIG. 3 shows hydrophobicity of the sheets of filter paper measured with the contact angle goniometer. Untreated paper (a) and paper treated on the surface with the post-enzymatic preparation (b).

Sheets of filter paper were treated by immersion in the functionalizing solutions (Table 1) and they were compared to the untreated paper with respect to the contact angle (CA) between the water and the surface of paper. The contact angle is a method which gives a general idea as to the hydrophobicity of a surface. It is generally assumed that if the contact angle is less than 90°, the surface is hydrophilic, whereas if this angle is greater than 90°, the surface is hydrophobic. Measurements were taken using a contact angle goniophotometer, placing a 4 µL drop on the surface of paper, and obtaining a contact angle of around 18° for untreated paper and in the order of 130° for paper treated with the post-enzymatic preparations (FIG. 3).

The experience with papers obtained showed that for the treated papers, the water drop remained on the surface of the paper for a longer time period before it completely disappeared. For this reason, progression of the contact angle over time was monitored. Changes in the contact angle after placing the drop were due to the decrease in its volume and can basically be caused by 2 phenomena: absorption into the structure of the sheet and evaporation. Evaporation becomes a factor when the disappearance of the drop occurs over long time periods.

Figure 4:
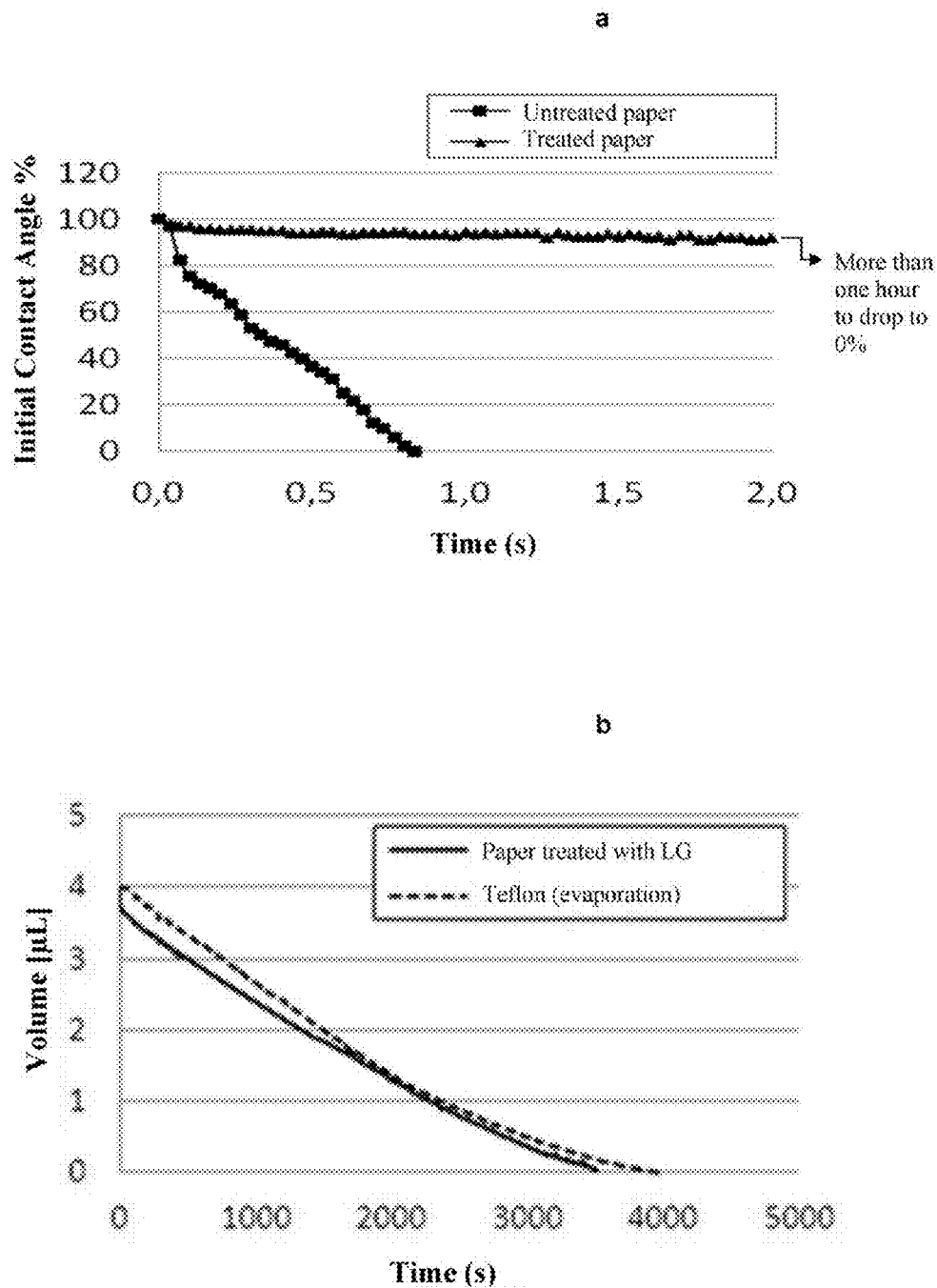
FIG. 4 shows variation of the contact angle over time for the treated and untreated filter paper (a) and the comparison of the absorption-evaporation with respect to the treated paper and TEFLON® (b).

Measurements of the contact angle were taken at a capture speed of 25 images/minute for 2 hours after placing the drop on the surface of paper. For filter paper without any surface treatment, the contact angle rapidly drops to 0° (less than a second), whereas for sheets treated with the functionalizing products, the contact angle takes up to one hour to drop to 0° (FIG. 4a).

Due to these long absorption times, which demonstrate a highly hydrophobic behavior, the treated sheets were compared to a sheet of TEFLON® as this is a non-absorbent material in which the disappearance of the volume of a water drop placed on the surface thereof is solely and exclusively due to evaporation. 4 µL of water were placed on the surface of both materials and the change in volume of the drop was monitored until said drop completely disappeared. FIG. 4b shows that the curves obtained are very similar, indicating that the most important phenomenon taking place in the treated paper is evaporation. Therefore, the sheets treated with the post-enzymatic products allow obtaining highly hydrophobic papers.

Treatment on Cellulosic Substrates. Modification of the Ionic Surface State of the Substrate.

Sheets of paper were made by means of a lab sheet-forming instrument from crude and ECF bleached eucalyptus Kraft pulp. Different compounds in a fibrous suspension that are capable of conferring a cationic nature to the sheets of paper were used when preparing said sheets (Table 3). The addition of said type of compounds is common practice in the process of manufacturing cellulosic substrates. Once the sheets of paper were obtained, the post-enzymatic solutions of Table 1 were applied.

TABLE 3

Compounds capable of conferring a cationic nature to the paper

| Compound | Dose |
|---|---|
| Wet-strength agent, PAAE resin | 0.7% of solids in fiber |
| Chitosan | 2% preparation |
| Cationic starch | 1% with respect to fiber weight |

Figure 5:
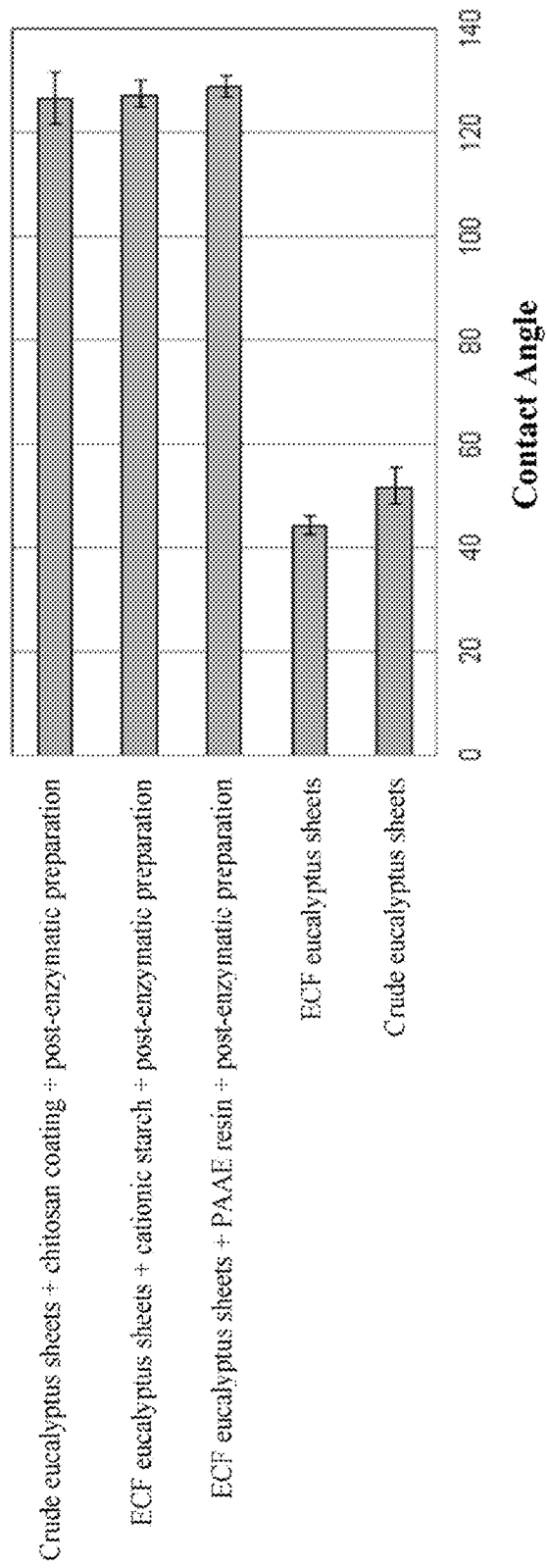
FIG. 5 shows the contact angle of the papers treated with compounds capable of making the sheets of paper cationic and subsequently functionalized by means of the post-enzymatic product.

Once the papers formed with the preceding compounds were impregnated with post-enzymatic preparation, they all showed high hydrophobicity indices. FIG. 5 shows the value of the contact angle for all the papers considered. It can be seen that the values of the contact angle obtained when the papers are treated with the different ionic state-modifying compounds and subsequently impregnated with the post-enzymatic product are similar.

Example 2

The present example illustrates maintaining and improving the physicomechanical properties of papers treated on the surface with the product illustrated in Example 1, consisting of a post-enzymatic product resulting from the reaction between a laccase enzyme of *Trametes villosa* and lauryl gallate (LG) as the phenol compound (solution D, Table 1). The surface treatments were performed on filter paper samples.

Physicomechanical Characterization

The papers used to evaluate the effect of the product of Example 1 on physicomechanical properties were commercial grade laboratory filter papers. Bendtsen air permeability (ISO 5636), bursting strength (ISO 2758), tearing resistance (ISO 1974), double folding endurance (ISO 5626), tensile strength (ISO 1924), wet tensile strength (ISO 3781), Cobb$_{60}$ sizing (ISO 535) and zero-span tensile strength (ISO 15361) were evaluated. At least ten repetitions were performed for each test, obtaining the mean value and standard deviation.

The sheets of untreated paper, the sheets treated only with solution at pH 4 (see Example 1), and the sheets treated with the post-enzymatic product described in Example 1 (solution D, Table 1) were evaluated.

Results

The obtained results are provided in detail in the following table:

TABLE 4

Physical properties of untreated papers, papers treated with solution at pH 4, and sheets treated with the post-enzymatic product described in Example 1 (solution D, Table 1)

|  | Untreated sheets | Sheets treated with solution at pH 4 | Sheets treated with post-enzymatic product |
|---|---|---|---|
| Burst index [kN/g] | 2.23 | 2.36 | 2.41 |
| Standard deviation | 0.23 | 0.31 | 0.25 |
| Tear index [mNm$^2$/g] | 12.36 | 11.58 | 11.95 |
| Standard deviation | 1.44 | 0.5 | 0.92 |
| Double fold [log no.] | 3 | 3 | 3 |
| Standard deviation | 0.3 | 0.1 | 0.1 |
| Tensile index [Nm/g] | 38.38 | 46.03 | 36.77 |
| Standard deviation | 5.43 | 3.23 | 4.06 |
| Wet tensile index [N] | 6.72 | 6.56 | 9.10 |
| Standard deviation | 0.73 | 0.83 | 2.55 |
| Cobb$_{60}$ [g/m$^2$] | — | — | 22 |
| Standard deviation | — | — | 2.07 |
| Zero-span [N/cm] | 73 | 85 | 79 |
| Standard deviation | 9 | 6 | 6 |

Table 4 shows how the results of the burst, tear, double fold, tensile and zero-span properties are of the same order and are not altered by use of the post-enzymatic product. Even the wet tensile and Cobb$_{60}$ sizing properties improve after surface application of the post-enzymatic product. In the case of Cobb$_{60}$ sizing, the untreated paper and the paper treated only with solution at pH 4 logically have such a high absorption of water that it was impossible to measure the Cobb$_{60}$ value, whereas the paper treated on the surface with the post-enzymatic product acquires such a highly hydrophobic nature that it is now possible to take the measurement. The wet tensile property increases by 35% with respect to the control. These results are of extreme interest because the substrate is made hydrophobic without jeopardizing the initial resistance properties.

Example 3

The present example illustrates obtaining a product consisting of a post-enzymatic preparation using a laccase enzyme differing from the two preceding examples, and lauryl gallate (LG) as the phenol compound. Said post-enzymatic product applied on the surface of the pre-formed or finished paper will increase the hydrophobic nature of said paper. The enzyme is a fungal laccase from a culture of *Cerrena unicolor* IBB303, produced by means of submerged fermentation. The tests were performed in cellulosic substrates of crude and ECF bleached eucalyptus Kraft pulp.

Doses and Conditions for Obtaining the Post-Enzymatic Product

The fungal enzyme from a culture of *Cerrena unicolor* IBB303 showed an activity of 1660 U/mL. In this case, treatments were performed in a 250 mL reactor, hermetically closed and stirred continuously. General reaction conditions were: pH 4, 0.12% of lauryl gallate (phenol compound), amount of surfactant 0.12%, which in this case was lignin sulfonate, temperature 40° C. and a 4-hour reaction time. After the reaction, the preparation was stored for subsequent use in surface functionalization. It should be pointed out that the phenol compound, LG, was disintegrated by means of ultrasounds as set forth in Example 1. Table 5 shows the doses used to obtain the post-enzymatic products.

TABLE 5

Treatment doses

| Treatment | Enzyme doses (mL) | Lauryl gallate doses (LG) (g) | Surfactant (lignin sulfonate) doses (g) | Water pH 4 doses (mL) |
|---|---|---|---|---|
| A | 0.102 | 0.06 | 0.00 | 49.94 |
| B | 0.102 | 0.06 | 0.06 | 49.88 |

Hydrophobicity Study

The Tappi standard T835 om-08 water drop test (WDT) explained in Example 1 was performed to determine hydrophobicity.

Application of the Post-Enzymatic Product. Modification of the Ionic Surface State of the Paper The post-enzymatic solutions of the treatment with lauryl gallate and the enzyme of *Cerrena unicolor* IBB303 (solutions, Table 5) were applied on cellulosic substrates obtained by means of a lab sheet-forming instrument. These cellulosic substrates were made from crude and ECF bleached eucalyptus Kraft pulp, and a wet-strength resin, PAAE, was used in the fibrous suspension to confer a cationic nature to the substrates as described in Example 1.

Results

The post-enzymatic solutions obtained according to Table 5 were applied on the surface of the substrate (in this case papers made from crude and ECF bleached eucalyptus Kraft pulp) and progression of the WDT was measured (as an indicator of the degree of hydrophobicity). Said surface application was performed by immersion. The WDT results are shown in Table 6.

TABLE 6

WDT of the impregnated samples

| Treatment | Absorption time (s) |
|---|---|
| A | 3770 |
| B | 4965 |

Even when applying the post-enzymatic product resulting from the reaction between lauryl gallate (LG) and the enzyme causes a significant increase in hydrophobicity (treatment A, Tables 5 and 6), it can be seen that the substantial increase in said property is clearly produced with the functionalizing product resulting from the reaction in the presence of the three elements, i.e., LG, surfactant and enzyme (treatment B, Tables 5 and 6).

The results in this example are consistent with those shown in Example 1, but with the difference that a different oxidative enzyme is used.

Example 4

The present example illustrates obtaining 4 different post-enzymatic products (using a laccase enzyme of *Trametes villosa* and 4 compounds) which, when applied on the surface of the pre-formed or finished substrate, will increase the antioxidant properties of said substrate.

Doses and Conditions for Obtaining the Post-Enzymatic Products

The enzyme used was the laccase of *Trametes villosa* with an activity of 588 U/mL.

The treatments were performed in a 250 mL reactor, hermetically closed and stirred continuously. General reaction conditions were: pH 4, 0.12% of hydrophobic compound, temperature 40° C. and a 4-hour reaction time. After the reaction, the preparation was stored for subsequent use in surface functionalization.

The compounds used to prepare the post-enzymatic products for the purpose of conferring antioxidant capacity to the substrates are the following:
2,4,6-tris(1-phenylethyl)phenol (tristyrylphenol)
3,4,5-trihydroxybenzoic acid octyl ester (octyl gallate)
dodecyl 3,4,5-trihydroxybenzoate (lauryl gallate)
(E)-3-(4-hydroxy-3-methoxyphenyl)prop-2-enoic acid (ferulic acid)

Study of the Antioxidant Capacity

A method developed by the Paper and Graphic Research Group of the UPC (Polytechnical University of Catalonia) based on the methods of Van den Berg et al. 1999 (9) and Serpen et al. 2007 (10) was used for the study of the antioxidant capacity. This test is based on quantifying discoloration of the ABTS* radical due to hydrogen or electron donor species interaction. The ABTS* radical cation is a chromophore absorbing at a wavelength of 415 nm, 654 nm or 754 nm and it is generated by an oxidation reaction of ABTS (2,2'-azino-bis(3-ethylbenzothiazoline-6-ammonium sulfonate)) with potassium persulfate.

Surface Application of the Post-Enzymatic Products

The post-enzymatic preparations were applied on the surface of cellulosic substrates. These cellulosic substrates were made in a lab sheet-forming instrument from crude and ECF bleached eucalyptus Kraft pulp using a wet-strength resin in fibrous suspension, as described in Example 1.

Results

The following table shows the measurements of the progression of antioxidant capacity as a percentage of inhibition (discoloration) of the ABTS* radical cation of the substrates treated with the different post-enzymatic products according to the phenol compound used when preparing the functionalizing product. A higher percentage of inhibition means greater antioxidant capacity.

TABLE 7

Antioxidant capacity of the substrates impregnated with the different functionalizing products

| Treatment | Compound | % of inhibition |
|---|---|---|
| A | — | 5 |
| B | Tristyrylphenol | 89 |
| C | Octyl gallate | 99 |
| D | Lauryl gallate | 73 |
| E | Ferulic acid | 74 |

Table 7 clearly shows that the paper by itself does not have any antioxidant capacity (treatment A, Table 7), whereas the substrate treated with the different post-enzymatic products increases its power of inhibiting ABTS* radical cation in a range going from 73% to 99%. Treatment with the octyl gallate compound (treatment C, Table 7), which obtained a virtually complete inhibition power, should be pointed out.

The study can be extended to other compounds susceptible to showing antioxidant capacity.

Example 5

The present example illustrates obtaining two post-enzymatic products consisting of preparations (using a fungal laccase enzyme from a culture of *Cerrena unicolor* IBB303 and two compounds) which, when applied on the surface of the pre-formed or finished substrate, will increase the antioxidant properties of said substrate. An enzyme different from the one in Example 4 was used in this example.

Doses and Conditions for Preparing the Post-Enzymatic Products

The enzyme used was fungal laccase from a culture of *Cerrena unicolor* IBB303 with an activity of 1660 U/mL.

The treatments were performed in a 250 mL reactor, hermetically closed and stirred continuously. General reaction conditions were: pH 4, 0.12% of phenol compound, temperature 40° C. and a 4-hour reaction time. After the reaction, the preparation was stored for subsequent use in surface functionalization.

Two compounds for conferring antioxidant capacity to the substrates were selected based on the results of the preceding examples, and these compounds were:
3,4,5-trihydroxybenzoic acid octyl ester (octyl gallate)
dodecyl 3,4,5-trihydroxybenzoate (lauryl gallate) (this compound also provides hydrophobic properties)

Study of the Antioxidant Capacity

The method described in Example 4 was used for the study of the antioxidant capacity.

Surface Application of the Post-Enzymatic Products

The previous two post-enzymatic solutions were applied on cellulosic substrates. Said cellulosic substrates were made in a lab sheet-forming instrument from crude and ECF bleached eucalyptus Kraft pulp and were pre-treated using a wet-strength resin in fibrous suspension, as described in Example 1.

Results

The following table shows the measurement of the progression of antioxidant capacity as a percentage of inhibition (discoloration) of the ABTS* radical cation of the papers treated with the different post-enzymatic solutions.

TABLE 8

Antioxidant capacity of the sheets impregnated with the octyl gallate and lauryl gallate products

| Treatment | Compound | % of inhibition |
|---|---|---|
| A | — | 5 |
| B | Octyl gallate | 57 |
| C | Lauryl gallate | 83 |

Table 8 shows that the substrate treated with the post-enzymatic product derived from the reaction between the fungal enzyme from a culture of *Cerrena unicolor* IBB303 and the compound lauryl gallate (treatment C, Table 8) conferred high antioxidant power, in the order of 83% inhibition power of the ABTS* radical cation. In the case of octyl gallate (treatment B, Table 8), a lower inhibition power was obtained, in the order of the 57%, but it is still high nonetheless when compared to the paper without surface treatment (treatment A, Table 8).

These results demonstrate that it is possible to use different enzymes for obtaining post-enzymatic products which, when applied on the substrate, confer antioxidant power to said substrate.

Comparative Example 6

The present example illustrates obtaining a post-enzymatic product consisting of a preparation using a laccase enzyme of *Trametes villosa* and lauryl gallate (LG) as the hydrophobic compound. Said product is obtained from the same initial compounds that are used in patent WO 2011/009979 A1 for the purpose of functionalizing individual cellulose fibers (in aqueous suspension). Nevertheless, said compounds are reacted in the absence of cellulose fibers in the present patent application for the purpose of subsequently applying them (once the enzymatic reaction has ended) on the surface of a pre-formed cellulosic substrate or sheet to achieve functionalization thereof.

The purpose of the present example is to see if treating individual cellulose fibers using the post-enzymatic product in fibrous suspension can also increase hydrophobicity of the paper obtained from said fibers in a manner similar to when it is applied on the surface.

Doses and Conditions for Obtaining the Post-Enzymatic Product

The enzyme used was the laccase of *Trametes villosa* with an activity of 588 U/mL.

In this specific case, treatments were performed in a 250 mL reactor, hermetically closed and stirred continuously. General reaction conditions were: pH 4, 0.12% of lauryl gallate (hydrophobic compound), amount of surfactant 0.12%, which in this case was lignin sulfonate, temperature 40° C. and a 4-hour reaction time. After the reaction, the preparation was stored for subsequent use in surface functionalization.

The ultrasonic disintegration described in previous examples is used in this example to break up the LG aggregates before the enzymatic reaction. As a result of applying ultrasounds, LG is homogenously distributed throughout the reaction medium.

Treatment of Cellulose Fibers with the Post-Enzymatic Product and Subsequent Production of Sheets of Paper Eucalyptus cellulose fibers (ECF) were treated, keeping them in suspension in the post-enzymatic product by means of stirring for 10 minutes, and at a consistency of 3%. The suspension was then diluted to take it to a consistency of 0.24% for manufacturing laboratory sheets of paper, standardized according to ISO 5269-2:2004 by means of a Rapid-Köten lab sheet-forming instrument.

Hydrophobicity Study

The Tappi standard T835 om-08 water drop test (WDT) was performed to determine the hydrophobicity of the papers obtained in a simple manner. This test consists of applying a distilled water drop by means of a syringe and measuring the time it takes to be adsorbed by the paper.

The initial contact angle between a water drop and the surface of treated papers and a model of the absorption-evaporation of the water drop in the structure of the paper were also analyzed.

Results

It was seen that the hydrophobicity obtained in the papers manufactured from the fibers treated with the post-enzymatic product and measured by means of WDT was less than one second, meaning that the papers obtained have no hydrophobicity whatsoever with respect to absorption of water. The sheets of paper obtained from untreated eucalyptus fibers (ECF) also showed a WDT value of less than one second.

The sheets of paper obtained from eucalyptus fibers (ECF) treated in fibrous suspension with the post-enzymatic product and manufactured by means of the Rapid-Köten lab sheet-forming instrument were compared to sheets obtained from untreated eucalyptus fibers (ECF) with respect to the contact angle (CA) between the water and the surface of paper. The contact angle obtained was around 23° for the paper obtained from untreated eucalyptus fibers (ECF), and in the order of 29° for the paper obtained from eucalyptus fibers (ECF) treated in fibrous suspension with the post-enzymatic product. The contact angles obtained indicated that the sheets of paper showed no type of hydrophobic character when the fibers were treated in aqueous suspension with the post-enzymatic product. The difference between the contact angles observed between the paper obtained from treated fibers and the paper obtained from untreated fibers is not significant, and it can be asserted that treating the fibers in aqueous suspension with the post-enzymatic product does not increase hydrophobicity of the sheets.

Generally, and based on the results of the present example, it can be concluded that applying the post-enzymatic product on the cellulose fibers in fibrous suspension is not able to confer hydrophobicity to said fibers; therefore, it is not able to confer hydrophobicity to the paper formed from said fibers either. However, when the product is applied on the surface of pre-formed sheets of paper, the product is able to confer a hydrophobic character to them as set forth in the preceding examples.

LITERATURE

1. NEIMO, L. Papermaking science and technology, Vol. 4. Papermaking chemistry Finland: Finnish paper engineers' and Tappi Faper Oy, 1999 *Internal Sizing of Paper.*, pp. 151-203.
2. HUBBE, M. Paper's Resistance to Wetting—A Review of Internal Sizing Chemicals and their Effect, 2007, vol. Bioresources 2, no. 1. pp. 106-145 ISSN 19302126.
3. Hossain, H., Uddin, M., Saifullah, K., Rashid, M., Mollah, M. Hydrophobic Property of Handmade Jute Paper Treated by Sizing Material 'Rosin'. *Daffodil International University Journal of Science and Technology*, 2010, vol. 5, no, 1.
4. MURAT, O. and JOHN D, F. *Active Food Packaging Technologies.*—Taylor & Francis, 10 Aug. 2010, 2010 ISBN—1040-8398. DOI—10.1080/10408690490441578.
5. GARCIA-UBASART, J., et al. Enzymatic Treatments of Pulp using Laccase and Hydrophobic Compounds. *Bioresource Technology*, 2011, vol. 102, no. 3. pp. 2799-2803 ISSN 0960-8524.
6. ARACRI, E., COLOM, J. F. and VIDAL, T. Application of Laccase-Natural Mediator Systems to Sisal Pulp: An Effective Approach to Biobleaching Or Functionalizing Pulp Fibers?. *Bioresource Technology*, 2009, vol. 100, no. 23. pp. 5911-5916 ISSN 0960-8524.
7. KUDANGA, T., et al. Laccase-Mediated Wood Surface Functionalization. *Engineering in Life Sciences*, 2008, vol. 8, no. 3. pp. 297-302 ISSN 1618-0240.
8. HOSSAIN, K. M. G., GONZALEZ, M. D., JUAN, A. R. and TZANOV, T. Enzyme-Mediated Coupling of a Bi-Functional Phenolic Compound Onto Wool to Enhance its Physical, Mechanical and Functional Properties. *Enzyme and Microbial Technology*, 2010, vol. 46, no. 3-4. pp. 326-330 ISSN 0141-0229.
9. VAN DEN BERG, R., HAENEN, G. R. M. M., VAN DEN BERG, H. and BAST, A. Applicability of an Improved Trolox Equivalent Antioxidant Capacity (TEAC) Assay for Evaluation of Antioxidant Capacity Measurements of Mixtures. *Food Chemistry*, 9, 1999, vol. 66, no. 4. pp. 511-517 ISSN 0308-8146.
10. SERPEN, A., CAPUANO, E., FOGLIANO, V. and GÖKMEN, V. A New Procedure to Measure the Antioxidant Activity of Insoluble Food Components. *Journal of Agricultural and Food Chemistry*, 2007, vol. 55, no. 19. pp. 7676-7681 SCOPUS.

The invention claimed is:

1. A method for functionalizing a surface of a paper or cellulosic substrate, the method comprising:
   contacting an isolated aqueous enzymatic preparation with a surface of paper or a cellulosic substrate by a surface application technique comprising immersion-impregnation, spraying, size press or metering bar,
   wherein the isolated aqueous enzymatic preparation is prepared by reacting at least one oxidoreductase enzyme with at least one compound that is a substrate for the enzyme in an aqueous solution, wherein said at least one compound comprises, in the structure thereof, at least one phenol or alcohol group, which optionally has one or more hydrophobic chains, or at least one sterol group, and wherein the reaction is performed in the absence of an external agent, said external agent being cellulosic fibers, wherein the isolated enzymatic preparation contains the at least one oxidoreductase and the resultant product obtained by said reaction in the aqueous solution.

2. The method according to claim 1, wherein the aqueous enzymatic preparation is contacted with the surface of the paper or cellulosic substrate in a step of: in a forming area, in a drying section, in a size press, in a coating area, in an end product, or between said contacting steps.

3. The method according to claim 1, wherein the paper or cellulosic substrate at least includes a substrate obtained from wood and non-wood fibers, bleached and non-bleached fibers, mechanical, chemical and semi-chemical pulps, recycled fibers, cellulose microfiber films, cellulose nanofiber films, nanocellulose crystals or lignin films.

4. The method according to claim 1, further comprising modifying the surface of the paper or cellulosic substrate by contacting the surface of the paper or cellulosic substrate with cation products comprising cationic polyamidoamine-epichlorohydrin (PAAE) resins, chitosan or cationic starch, thereby aiding in fixing of the isolated aqueous enzymatic preparation on the surface of the paper or cellulosic substrate.

5. The method according to claim 1, wherein the compound is represented by the following structure:

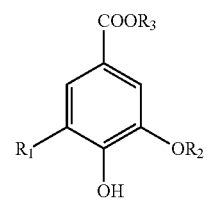

where $R_3$ is —H or an alkyl$\geq C_1$, and $R_1$, $R_2$ is:
   i) $R_1$=—OH and $R_2$=—H;
   ii) $R_1$ and $R_2$=—H, 3,4-dihydroxy-benzoic acid esters; or
   iii) $R_1$=—H and $R_2$=—CH$_3$, vanillic acid esters.

6. The method according to claim 1, wherein the compound is represented by the following structure:

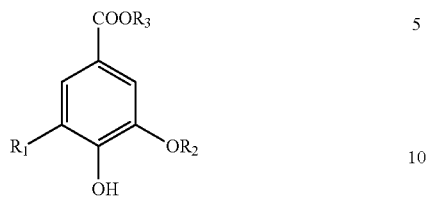

where $R_3$ is —H or an alkyl between $C_1$ and $C_{34}$, and $R_1$, $R_2$ is:
 i) $R_1$=—OH and $R_2$=—H;
 ii) $R_1$ and $R_2$=—H, 3,4-dihydroxy-benzoic acid esters; or
 iii) $R_1$=—H and $R_2$=—CH$_3$, vanillic acid esters.

7. The method according to claim 1, wherein a lignin sulfonate surfactant is included with the oxidoreductase enzyme and compound during the reaction to prepare the isolated aqueous enzymatic preparation.

8. The method according to claim 1, wherein said reaction is performed at a pH between 4 and 7 and at a temperature between 30° C. and 60° C.

* * * * *